United States Patent
Hell

(10) Patent No.: US 9,267,888 B2
(45) Date of Patent: Feb. 23, 2016

(54) METHOD OF SPATIAL HIGH RESOLUTION IMAGING OF A STRUCTURE OF A SAMPLE, THE STRUCTURE COMPRISING A LUMINOPHORE

(71) Applicant: Max-Planck-Gesellschaft zur Foerderung der Wissenschaften e.V., Munich (DE)

(72) Inventor: Stefan W. Hell, Goettingen (DE)

(73) Assignee: MAX-PLANCK-GESELLSCHAFT ZUR FOERDERUNG DER WISSENS, Munich (DE)

( * ) Notice: Subject to any disclaimer, the term of this patent is extended or adjusted under 35 U.S.C. 154(b) by 0 days.

(21) Appl. No.: 14/791,932

(22) Filed: Jul. 6, 2015

(65) Prior Publication Data

US 2015/0308955 A1 Oct. 29, 2015

Related U.S. Application Data

(63) Continuation of application No. PCT/EP2014/050272, filed on Jan. 9, 2014.

(30) Foreign Application Priority Data

Jan. 9, 2013 (DE) .......................... 10 2013 100 172

(51) Int. Cl.
  *F21V 9/16* (2006.01)
  *G01N 21/64* (2006.01)
  *G01N 21/65* (2006.01)

(52) U.S. Cl.
  CPC ............ *G01N 21/64* (2013.01); *G01N 21/6428* (2013.01); *G01N 21/6458* (2013.01);
  (Continued)

(58) Field of Classification Search
  CPC .................. G01N 21/6458; G01N 2021/6421; G01N 2021/6419
  See application file for complete search history.

(56) References Cited

U.S. PATENT DOCUMENTS 5,731,588 A * 3/1998 Hell et al. .................. 250/458.1
7,064,824 B2 * 6/2006 Hell .............................. 356/317
(Continued)

FOREIGN PATENT DOCUMENTS

DE 10 2006 011 176 A1 9/2007
DE 10 2006 026 204 A1 12/2007
(Continued)

OTHER PUBLICATIONS

PCT International Preliminary Report on Patentability in co-pending, related PCT Application No. PCT/EP2014/050272, mailed Jul. 14, 2015.
(Continued)

*Primary Examiner* — David J Makiya
*Assistant Examiner* — Kenneth J Malkowski
(74) *Attorney, Agent, or Firm* — Thomas | Horstemeyer, LLP

(57) ABSTRACT

For spatial high resolution imaging of a structure of a sample comprising a luminophore, the sample is subjected to excitation inhibiting light transferring the luminophore out of an excitable electronic ground state into a protection state in which the luminophore is protected against electronic excitation by luminescence excitation light and luminescence de-excitation light. The excitation inhibiting light comprises a first local minimum. Next, the sample is subjected to the luminescence excitation light exciting the luminophore within the first local minimum into an excited luminescent state. Then, the sample is subjected to the luminescence de-excitation light returning the luminophore out of the excited luminescent state into the excitable electronic ground state. The luminescence de-excitation light comprises a second local minimum overlapping with the first local minimum. Luminescence light emitted out of the measurement area is measured and assigned to the position of the second local minimum within the sample.

20 Claims, 2 Drawing Sheets

(52) U.S. Cl.
CPC ........ *G01N21/65* (2013.01); *G01N 2021/6419* (2013.01); *G01N 2021/6421* (2013.01); *G01N 2201/061* (2013.01)

(56) References Cited

U.S. PATENT DOCUMENTS

| | | | |
|---|---|---|---|
| 7,709,809 | B2 | 5/2010 | Kempe et al. |
| 8,207,510 | B2 | 6/2012 | Kempe et al. |
| 8,399,857 | B2 | 3/2013 | Lippert |
| 9,024,279 | B2 | 5/2015 | Hell |
| 2007/0206278 | A1* | 9/2007 | Dyba et al. .................. 359/385 |
| 2008/0007730 | A1 | 1/2008 | Kempe et al. |
| 2009/0242801 | A1* | 10/2009 | Engelhardt et al. ........ 250/459.1 |
| 2011/0182529 | A1 | 7/2011 | Kempe et al. |
| 2012/0100559 | A1 | 4/2012 | Hell et al. |
| 2012/0104279 | A1 | 5/2012 | Reuss et al. |

FOREIGN PATENT DOCUMENTS

| | | |
|---|---|---|
| DE | 10 2006 046 369 A1 | 4/2008 |
| DE | 10 2006 047 912 A1 | 4/2008 |
| DE | 10 2008 049 878 A1 | 4/2010 |
| DE | 10 2010 028 138 A1 | 10/2011 |

OTHER PUBLICATIONS

Grot, Johann, et al., "rsEGFP"enables fast RESOLFT nanoscopy of living cells, ELIFE, vol. 1, No. 0, Jan. 1, 2012, pp. e00248, XP055115522, DOI.

PCT International Search Report in co-pending, related PCT Application No. PCT/EP2014/050272, mailed May 9, 2014.

* cited by examiner (a)

(b)

(c)

(d)

US 9,267,888 B2

METHOD OF SPATIAL HIGH RESOLUTION IMAGING OF A STRUCTURE OF A SAMPLE, THE STRUCTURE COMPRISING A LUMINOPHORE

CROSS REFERENCE TO RELATED APPLICATIONS

The present invention is a continuation of International Patent Application PCT/EP2014/050272 filed on Jan. 9, 2014, entitled "Method for spatially high-resolved imaging of a structure of a sample that has a luminophore" and claiming priority to German Patent Application DE 10 2013 100 172.6, filed Jan. 9, 2013, entitled "Verfahren zum räumlich hochauflösenden Abbilden einer einen Luminophor aufweisenden Struktur einer Probe".

FIELD OF THE INVENTION

The invention relates to a method of spatial high resolution imaging of a structure of a sample, the structure comprising a luminophore. More particular, the invention relates to a method of spatial high resolution imaging of a structure of a sample, the structure comprising a luminophore, wherein the sample, in a measurement area, is subjected to luminescence excitation light which excites the luminophore out of an excitable electronic ground state into an excited luminescent state, wherein the sample, in the measurement area, is subjected to an intensity distribution of luminescence de-excitation light comprising a local minimum, which returns the luminophore out of the excited luminescent state into the excitable electronic ground state, wherein luminescence light emitted out of the measurement area is registered, and wherein the registered luminescence light is assigned to the position of the local minimum within the sample.

BACKGROUND

A method of spatial high resolution imaging of a structure of a sample, the structure comprising a luminophore, is known as STED (Stimulated Emission Depletion) scanning fluorescence light microscopy. Here, the sample, in the measurement area, is at first subjected to the luminescence excitation light which excites the luminophore out of the excitable electronic ground state into the excited luminescent state. Then, the sample, in the measurement area, is subjected to an intensity distribution of the luminescence de-excitation light in the form of emission stimulation light which stimulates the luminophore for emission of light having the wavelength of the emission stimulation light, i.e. a different wavelength than that one of the luminescence light, and thus de-excites it back into its ground state, the intensity distribution having a local minimum. If the luminescence de-excitation light de-excites the luminophore out of the excited luminescent state everywhere outside the local minimum by means of stimulated emission, the luminescence light emitted out of the measurement area afterwards may only stem from the local minimum of the intensity distribution of the luminescence de-excitation light and may thus be assigned to the position of the local minimum within the sample.

In the method known as STED, a very high spatial resolution at a high contrast in imaging a structure of a sample, the structure being marked with a luminophore, is also achieved in practice. Here, however, the luminophore is seriously stressed photochemically and thus tends to bleaching. The reason is that the luminescence de-excitation light, which has to be applied at a high absolute intensity to narrow down the local minimum in the form of a zero point of its intensity distribution, is applied to the luminophore already being in its excited luminescent state. Thus, besides the desired stimulated emission which returns the luminophore into its ground state, other processes, particularly further electronic excitations of the luminophore resulting into bleaching, are also not unlikely. New excitations of the luminophore at first de-excited by stimulated emission may also occur due to the light originally provided for luminescence de-excitation.

A further method of spatial high resolution imaging of a structure of a sample, the structure comprising a luminophore, is known as GSD (Ground State Depletion) scanning fluorescence light microscopy. In this known method, the luminophore, prior to being subjected to the luminescence excitation light, is subjected to luminescence inhibiting light which has an intensity distribution comprising a local minimum. The luminescence inhibiting light transfers the luminophore into a dark state, like for example a long living triplet state, out of which it is not excited into a luminescent state by means of the luminescence excitation light. Everywhere outside the local minimum of the intensity distribution of the luminescence inhibiting light, this transfer into the dark state is saturated. I.e. only in the local minimum of the intensity distribution of the luminescence inhibiting light, the luminophore, after being subjected to the luminescence inhibiting light, is still in its electronic ground state out of which it is excited into the luminescent state by the luminescence excitation light. Luminescence light emitted by the luminophore after excitation by the luminescence excitation light thus stems from the local minimum of the intensity distribution of the luminescence inhibiting light and may thus be assigned to the position of the local minimum within the sample.

In the method known as GSD, there is a considerable danger of bleaching the luminophore as well, because the luminophore, in its long-living dark state, into which it is transferred by the luminescence inhibiting light, has an increased tendency to chemical reactions like, for example, with oxygen, and/or it is exposed to the danger that it is further excited by the luminescence inhibiting light or the luminescence excitation light so that a photochemical bleaching of the luminophore occurs.

A further method of spatial high resolution imaging of a structure of a sample, the structure comprising a luminophore, is known as a variant of RESOLFT (Reversible Saturable Optical Fluorescence Transitions) scanning fluorescence light microscopy which makes use of so-called switchable luminophores. By means of luminescence inhibiting light, these luminophores are switchable out of a first conformation state in which they are acting as luminophores into a second conformation state in which they are not acting as luminophores, i.e. in which they are, at least by means of the luminescence excitation light which is usable for exciting the luminescent state in the first conformation state, not excitable into the luminescent state in which they emit the luminescence light registered as the measurement signal. With a sufficient long lifetime of the second conformation state, only comparatively low light intensities are necessary to saturate this switching everywhere outside a local minimum of the intensity distribution of the luminescence inhibiting light. Further, there is no significant danger that the luminophore transferred into its other conformation state bleaches out of this other conformation state as it does not respond to the luminescence inhibiting light or the luminescence excitation light within this conformation state.

In the practical implementation of RESOLFT scanning fluorescence light microscopy with switchable fluorophores, a spatial resolution and a contrast are observed which lag behind those of STED scanning fluorescence light microscopy. This may be due to the fact that even then when the switching of the switchable luminophore into a conformation state not capable of luminescence is saturated, there is still a noticeable percentage of the luminophore in its conformation state capable of luminescence.

There still is a need of a method of spatial high resolution imaging of a structure of a sample, the structure comprising a luminophore, in which the high spatial resolution and the high contrast of STED scanning fluorescence light microscopy are achieved and in which the luminophore is nevertheless subjected to a lower danger of photochemical bleaching than in all previously known methods of STED scanning fluorescence light microscopy.

SUMMARY OF THE INVENTION

In one aspect, the present invention relates to a method of high spatial resolution imaging of a structure of a sample, the structure comprising a luminophore. In a measurement area, the method comprises subjecting the sample to an intensity distribution of excitation inhibiting light transferring the luminophore out of an excitable electronic ground state into a protection state in which the luminophore is protected against electronic excitation by luminescence excitation light and by luminescence de-excitation light, the intensity distribution of the excitation inhibiting light comprising a first local minimum; subjecting the sample to the luminescence excitation light exciting the luminophore which, within the first local minimum of the intensity distribution of the excitation inhibiting light, is still in its excitable electronic ground state into an excited luminescent state; subjecting the sample to an intensity distribution of the luminescence de-excitation light returning the luminophore out of the excited luminescent state into the excitable electronic ground state, the intensity distribution of the luminescence de-excitation light comprising a second local minimum overlapping with the first local minimum of the intensity distribution of the excitation inhibiting light; registering luminescence light emitted out of the measurement area; and assigning the registered luminescence light to the position of the second local minimum of the intensity distribution of the luminescence de-excitation light within the sample.

In another aspect, the present invention relates to a method of high spatial resolution imaging of a structure of a sample, the structure comprising a luminophore. This method, in addition to the above steps of subjecting, registering and assigning, comprises scanning the sample with the second local minimum of the intensity distribution of the luminescence de-excitation light; and repeating the above steps of subjecting registering and assigning for a plurality of positions of the second local minimum of the intensity distribution of the luminescence de-excitation light within the sample.

In the method according to the invention, the intensity of the luminescence light emitted out of the measurement area is a measure of the concentration of the luminophore at the position of the local minimum within the sample. By scanning the sample with the local minimum, while repeating the above mentioned steps for each position of the local minimum, the distribution of the luminophore in the sample is determined, and, thus, the structure marked with the luminophore is imaged.

Here, the term "luminophore" designates any substance from which luminescence light may be obtained as a measurement signal, if it is in an excited luminescent state. This definition particularly applies to fluorescence dyes. The process on which the emission of the luminescence light is based, however, does not need to be fluorescence. It may also be scattering, like for example Raman scattering, in which the excited transitional states out of which the scattered light is emitted are regarded as the excited luminescent states here.

The structure of interest of the sample may comprise the luminophore as such, i.e. it may be autoluminescent. The structure of interest of the sample, however, may also be artificially marked with the luminophore. This artificial marking of the structure with the luminophore may, for example, be executed by so-called antibody dyeing, i.e. by coupling the luminophore via an immunoreaction, or by means of genetic engineering resulting in a simultaneous expression of the luminophore and the structure of interest.

If a state, like for example an excitable electronic ground state or an excited luminescent state of the luminophore, is mentioned here, this is an electronic state of the smallest entity of the luminophore capable of luminescence, i.e. of a molecule, of a complex, of a void, of a quantum dot or the like.

If a local minimum of an intensity distribution of light, like for example the luminescence de-excitation light, is mentioned here, this particularly means a zero point of the intensity distribution created by interference. It may be a true zero point in which the intensity of the light in fact goes down to zero, or a zero point in which the intensity of the light in the absence of ideal optical conditions only essentially goes down to zero. If dimensions of a local minimum are mentioned here, these dimensions particularly relate to the dimensions of the volume in which the respective light does not saturate the effect strived for by the respective light, like for example the transfer excited by the respective light.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
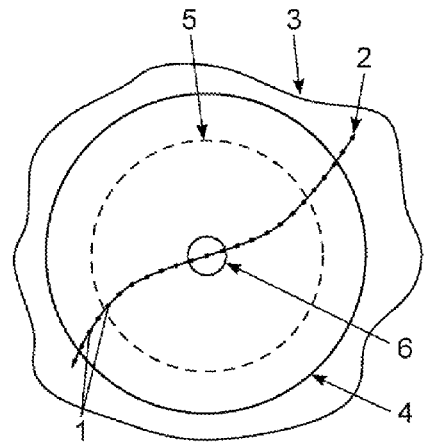
FIG. 1 (*a*) to (*d*) illustrate the method steps of a method according to the invention of spatial high resolution imaging of a structure of a sample, the structure comprising a luminophore.
Figure 1:
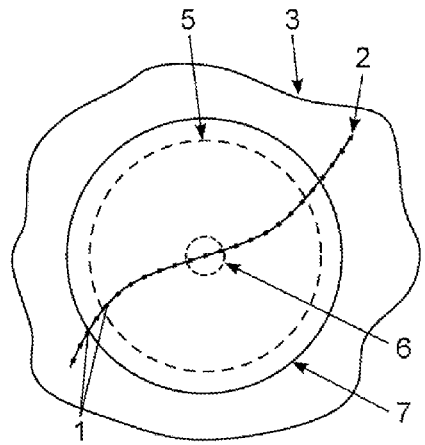
Figure 1:
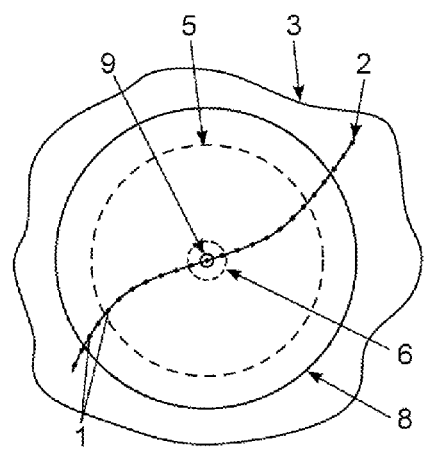
Figure 1:
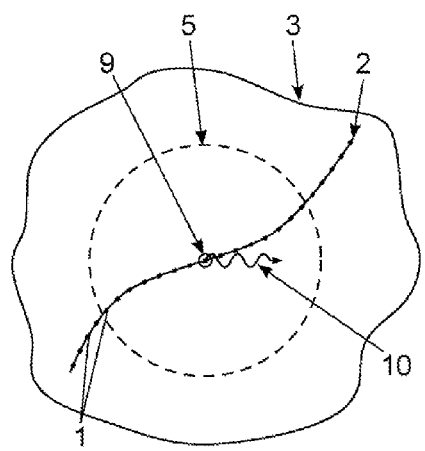

In a method according to the present invention of spatial high resolution imaging of a structure of a sample, the sample comprising a luminophore, all steps are carried out which are characteristic of an STED scanning fluorescence light microscopic method; i.e. the method according to the invention is a special method of STED scanning luminescence light microscopy: The sample, in a measurement area, is subjected to luminescence excitation light which excites the luminophore out of an excitable electronic ground state into an excited luminescent state. In the measurement area, the sample is further subjected to an intensity distribution of luminescence de-excitation light comprising a local minimum, which, without emission of luminescence light, returns the luminophore out of the excited luminescent state into the excitable electronic ground state. Luminescence light emitted out of the measurement area is registered; and the registered luminescence light is assigned to the position of the local minimum in the sample.

In the method according to the invention, the sample, in the measurement area, prior to being subjected to the luminescence excitation light, is additionally subjected to an intensity distribution of excitation inhibiting light which transfers the luminophore out of the excitable electronic ground state into a protection state. Within this protection state the luminophore is protected against electronic excitations by the luminescence excitation light and the luminescence de-excitation light. The intensity distribution of the excitation inhibiting light also has a local minimum which overlaps with the local minimum of the intensity distribution of the luminescence de-excitation light.

The method according to the invention thus also includes the steps which are applied in a RESOLFT scanning fluorescence light microscopic method using a switchable luminophore. In the method according to the invention, however, it is not primarily tried to enhance the effective point spread function in the sense of an increased spatial resolution by superimposing two intensity distributions which have a spatially resolving effect with coincident zero points. Instead, the method according to the invention primarily makes use of the fact that the luminophore, for example in a RESOLFT method using a switchable luminophore, outside the minimum of the intensity distribution of the excitation inhibiting light is transferred into a state in which it is not electronically excitable by the luminescence excitation light and the luminescence de-excitation light. This state is called the protection state of the luminophore here.

Even if, in the method according to the invention, the local minimum of the intensity distribution of the excitation inhibiting light is less sharply localized, i.e. larger than the local minimum of the intensity distribution of the luminescence de-excitation light, the excitation inhibiting light effectively inhibits the bleaching of the luminophore by the luminescence excitation light and the luminescence de-excitation light there, where they have their highest common intensity. This highest common intensity of the luminescence excitation light and the luminescence de-excitation light is not directly adjoining the local minimum of the intensity distribution of the luminescence de-excitation light but located at a certain distance thereto. At this distance to the local minimum of the intensity distribution of the luminescence de-excitation light, the transfer of the luminophore into its protection state is saturated, and thus the luminophore is protected against an electronic excitation and a resulting bleaching by the high common intensity of the luminescence excitation light and the luminescence de-excitation light, even with a little larger local minimum of the intensity distribution of the excitation inhibiting light.

There, where the high spatial resolution and finally also the high contrast are realized with the intensity distribution of the luminescence de-excitation light, i.e. directly adjoining the local minimum of the intensity distribution of the luminescence de-excitation light, the absolute intensity of the luminescence de-excitation light is much smaller than at a greater distance to the local minimum. The fact that at least a relevant part of the luminophore is not in its protection state here, does not essentially increase the risk of bleaching of the luminophore.

Thus, in the method according to the invention, the high spatial resolution and the high contrast which are achievable in STED scanning fluorescence light microscopy can be achieved without the massive danger of bleaching the luminophore, which is typical for previous STED methods. For this purpose, it is not necessary that the local minimum of the intensity distribution of the excitation inhibiting light is as small as the local minimum of the luminescence de-excitation light. Thus, it is also easier to overlap the local minimum of the intensity distribution of the excitation inhibiting light with the local minimum of the intensity distribution of the luminescence de-excitation light. I.e. a certain offset between the centers of these minima may be compensated for by a larger local minimum of the intensity distribution of the excitation inhibiting light.

It is to be understood that the luminescence excitation light, the luminescence de-excitation light and the excitation inhibiting light may have different wavelengths in the method according to the invention. Particularly, the wavelengths may be selected with regard to the absorption spectrum of the luminophore in such a way that the luminophore is only transferred or excited or de-excited by the respective light as desired and that none of the other transfers is triggered.

In the method according to the invention, the luminescence de-excitation light and the excitation inhibiting light may, however, also have same wavelengths and be applied to the sample simultaneously. I.e. the luminescence de-excitation light and the excitation inhibiting light may be the same light. Thus, in case of using a known switchable fluorescent protein, like for example rsEGFP or rsEGFP2, as the luminophore, a common wavelength of the excitation inhibiting light and the luminescence de-excitation light may be selected such that the light, outside the minimum of its intensity distribution, both by switching into its protection state not capable of luminescence at a certain first probability and by stimulating emission at a certain second probability, inhibits the luminophore in inhibiting luminescence light. Even in this procedure, there is a reduced danger of bleaching the luminophore as compared to a pure STED method which only uses stimulated emission for increasing the spatial resolution.

In the method according to the invention, the luminescence excitation light will normally be applied to the sample in pulses. The excitation inhibiting light and the luminescence de-excitation light may also be applied to the sample in pulses, or one or both of them may be applied to the sample continuously. Particularly, if the luminescence de-excitation light is applied continuously, it is advantageous to register the luminescence light at a temporal resolution after each pulse of the luminescence excitation light to maximize the spatial resolution and the contrast, like it is generally known from WO 2012/069076 A1 for an STED method.

In the method according to the invention, the excitation inhibiting light may transfer the luminophore out of its excitable electronic ground state into the protection state by means of a change in conformation. I.e. the luminophore, as already mentioned, may be a so-called switchable luminophore. Here, the properties of this switchable luminophore do not need to be ideal, like it would be essential for RESOLFT scanning fluorescence light microscopy in which the spatial resolution is based on the switchability of the luminophore. In the method according to the invention, the switchability of the luminophore is at least primarily not used for increasing the spatial resolution but for the protection of the luminophore against the high common intensities of the luminescence excitation light and the luminescence de-excitation light. This protection is essentially achieved already then, when the luminophore, by the excitation inhibiting light, is not completely but essentially transferred into its protection state. In other words, even switchable luminophores which could not suitably be used in a RESOLFT method based on switchable luminophores are usable in the method according to the invention.

The luminophore which may be switched off by the excitation inhibiting light may particularly be a switchable fluorescent protein as it is generally known to those skilled in the art.

The luminophore which can be switched off by means of the excitation inhibiting light may spontaneously return out of its protection state into the excitable electronic ground state. If such a spontaneous return does not occur or only occur at an insufficient rate of return, it is reasonable to subject the sample, in the measurement area, prior to subjecting it to the excitation inhibiting light, to an intensity distribution of excitation enabling light which transfers the luminophore, at least in the area of the local minimum of the intensity distribution of the luminescence de-excitation light, into the excitable electronic ground state in a defined way. Normally, this transfer takes place in the entire measurement area as the intensity distribution of the excitation enabling light, due to the diffraction barrier, cannot be focused further.

The method according to the invention, however, may not only be executed using switchable luminophores. For transferring the luminophore into its protection state, the excitation inhibiting light may instead, for example, disturb the excitable electronic ground state of the luminophore in such a way that the luminophore, in the protection state, has an absorption cross-section for the luminescence excitation light reduced by a factor of at least 2 as compared to the undisturbed electronic ground state. In this case, the protection state is the disturbed electronic ground state of the luminophore in which the disturbance, particularly the steric configuration of the atoms of the luminophore, significantly reduces its capability of interaction with the luminescence excitation light and preferably also with the luminescence de-excitation light. Such a disturbance of the electronic ground state of the luminophore may be caused by a transfer of impulses and/or vibrations. Such impulses and/or vibrations may come from a collisional or vibrational relaxation of a modulator entity excited by the excitation inhibiting light or from a cis-trans-isomerization of the modulator entity excited by the excitation inhibiting light. The modulator entity may be a molecule or a chemical group which is spatially and/or chemically coupled to the luminophore to ensure the desired transfer of impulse and/or vibration.

The disturbance of the electronic ground state of the luminophore, by which it is transferred into the protection state, may also be interpreted as increasing the vibration energy of the luminophore within its electronic ground state, this not being an energy state in thermal equilibrium with the surroundings of the luminophore. Instead, the energy of the luminophore, by means of the impulses and/or vibrations transferred by the modulator entity is increased above the thermal equilibrium with its surroundings. This disturbance of the ground state, which corresponds to the desired transfer of the luminophore into its protection state, gets lost again as soon as a thermal equilibrium between the luminophore and its surroundings is reached again due to further molecular transfers of impulses and/or vibrations. For the purpose of using the protection state in the form of the disturbed electronic ground state, the luminescence excitation light, and preferably also the luminescence de-excitation light, have to be applied to the sample while the disturbance of the electronic ground state of the luminophore still exists. Now referring in greater detail to the drawings, FIG. 1 (a) to (d) illustrate the steps of a method according to the invention of spatial high resolution imaging of a structure 2 of a sample 3, the structure comprising a luminophore 1. According to FIG. 1 (a), the sample 3 is subjected to excitation inhibiting light 4 which transfers the luminophore 1 into a protection state. This transfer takes place in a measurement area 5 of the sample except for a local minimum 6 of the intensity distribution of the excitation inhibiting light 4. In this local minimum 6, the luminophore 1 remains in its electronic ground state excitable for luminescence.

According to FIG. 1 (b), the sample 3, in the entire measurement area 5 including the local minimum 6, is subjected to luminescence excitation light 7 which transfers the luminophore 1, in so far as it is not in its protection state, out of its electronic ground state into an excited luminescent state. This means that only the luminophore 1 located in the area of the local minimum 6 of the excitation inhibiting light 4 is excited into the luminescent state.

According to FIG. 1 (c), the sample 3, in the measurement area 5, is subjected to luminescence de-excitation light 8, again except for a local minimum 9 of the intensity distribution of the luminescence de-excitation light 8 overlapping with the local minimum 6 of the excitation inhibiting light 4 according to FIG. 1 (a). The luminescence de-excitation light 8 transfers the luminophore 1, everywhere outside the local minimum 9 of its intensity distribution, out of its excited luminescent state back into its electronic ground state. Here, the local minimum 9 is smaller than the local minimum 6. I.e., where, after the step according to FIG. 1 (c), luminophore 1 is still in its luminescent state, depends on the position of the local minimum 9.

When luminescence light 10 out of the measurement area 5 is afterwards registered according to FIG. 1 (d), it may be assigned to the position of the local minimum 9 of the intensity distribution of the luminescence de-excitation light 8 according to FIG. 1 (c).

By scanning the sample with the measurement area 5 or with the local minimum 9, the distribution of the concentration of the luminophore 1 in the sample 3 is determined and thus the structure 2 in the sample is also imaged. To enable this scanning, the luminophore needs to quickly return into its excitable electronic ground state both out of its excited luminescent state and out of its protection state. If this does not apply to the protection state, the luminophore 1 may be subjected to excitation enabling light in the measurement area 5, which definedly transfers it back out of its protection state into its excitable electronic ground state prior to repeating the steps according to FIG. 1 (a) to (d) at the next position of the measurement area 5 or the local minimum 9.

Figure 2:
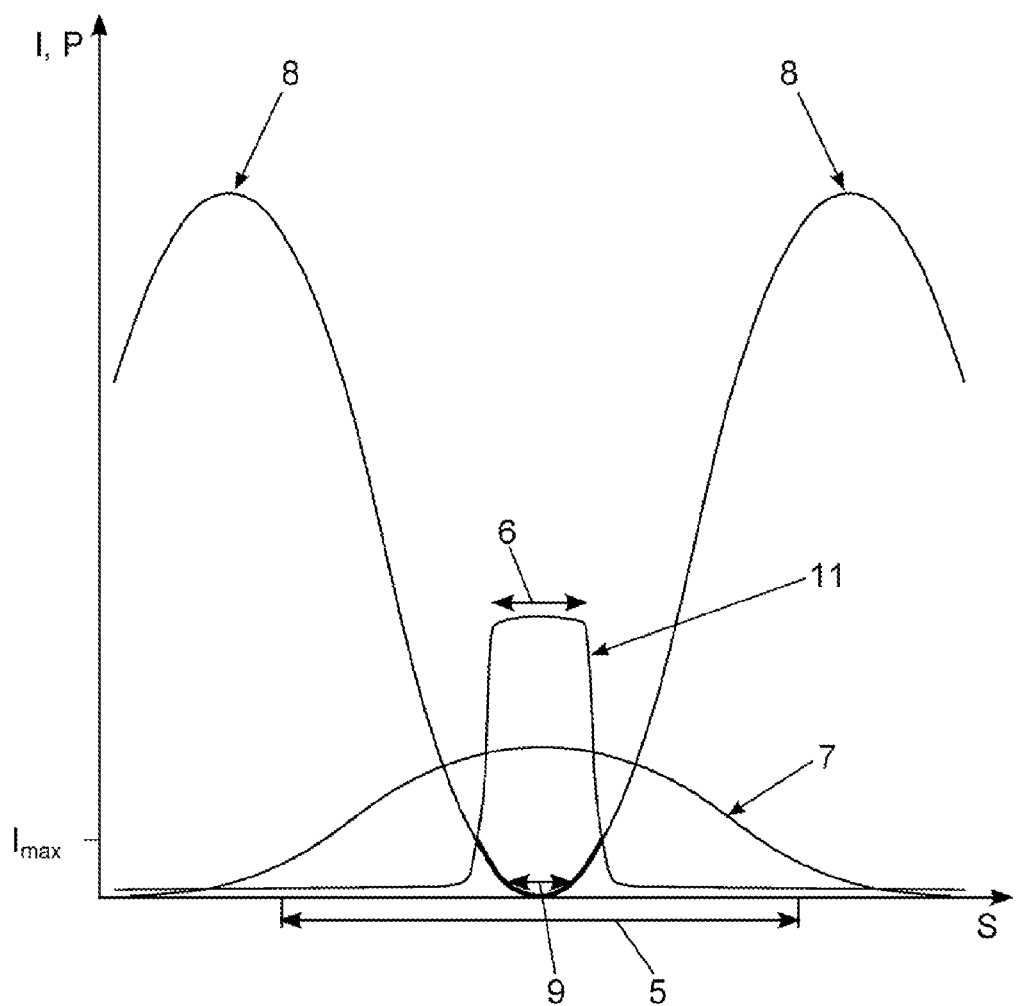
FIG. 2 illustrates the circumstances under which the sample is subjected to luminescence de-excitation light in step (c) of FIG. 1.

FIG. 2, in a cross-section through the measurement area 5, illustrates the intensity distributions of the luminescence excitation light 7 and the luminescence de-excitation light 8 as well as the probability 11 that the luminophore 1 after the subjection to the excitation inhibiting light 4 according to FIG. 1 (a) is still in its excitable electronic ground state, i.e. not in its protection state. Everywhere outside the local minimum 6 according to FIG. 1 (a), the probability 11 only has a low value which is close to zero. I.e. only within the local minimum 6, the luminophore is still in its excitable electronic ground state, and everywhere outside the local minimum 6 it is mostly likely in its protection state. The intensity distributions of the luminescence excitation light 7 and the luminescence de-excitation light 8 have their maximum common intensity outside the local minimum 6. I.e. the common maximum intensity hits the luminophore there, where it is in its protection state and will thus not be photochemically bleached. Within the local minimum 6, where the probability 11 is clearly higher than zero, besides the luminescence excitation light 7, only a low intensity of the luminescence de-excitation light 8 acts upon the luminophore, which does not exceed a value $I_{max}$ remaining far below the absolute maximum of this intensity. This low intensity is sufficient for the STED-typical narrowing down of the luminescent excited state of the luminophore to the local minimum 6 but not for the STED-typical bleaching of the luminophore which occurs at the high absolute common intensities of the luminescence excitation light 7 and the luminescence de-excitation light 8. Thus, in the method according to the invention, the high spatial resolution and the high contrast of an STED method are achieved but without accepting the danger of bleaching the luminophore which is usually connected therewith.

The spatial intensity distributions of the excitation inhibiting light 4 and the luminescence de-excitation light 8 about the local minima 6, 9 depicted here are only exemplary. These intensity distributions may have any arbitrary form in each spatial direction, as they are known from the field of STED scanning fluorescence light microscopy.

Many variations and modifications may be made to the preferred embodiments of the invention without departing substantially from the spirit and principles of the invention. All such modifications and variations are intended to be included herein within the scope of the present invention, as defined by the following claims.

The invention claimed is:

1. A method of high spatial resolution imaging of a structure of a sample, the structure comprising a luminophore, the method comprising
   in a measurement area, subjecting the sample to an intensity distribution of excitation inhibiting light transferring the luminophore out of an excitable electronic ground state into a protection state in which the luminophore is protected against electronic excitation by luminescence excitation light and by luminescence de-excitation light, the intensity distribution of the excitation inhibiting light comprising a first local minimum;
   in the measurement area, subjecting the sample to the luminescence excitation light exciting the luminophore which, within the first local minimum of the intensity distribution of the excitation inhibiting light, is still in its excitable electronic ground state into an excited luminescent state;
   in the measurement area, subjecting the sample to an intensity distribution of the luminescence de-excitation light returning the luminophore out of the excited luminescent state into the excitable electronic ground state, the intensity distribution of the luminescence de-excitation light comprising a second local minimum overlapping with the first local minimum of the intensity distribution of the excitation inhibiting light;
   registering luminescence light emitted out of the measurement area; and
   assigning the registered luminescence light to the position of the second local minimum of the intensity distribution of the luminescence de-excitation light within the sample.

2. The method of claim 1, wherein wavelengths of the luminescence excitation light, of the luminescence de-excitation light, and of the excitation inhibiting light are different.

3. The method of claim 1, wherein wavelengths of the luminescence de-excitation light and of the excitation inhibiting light are equal.

4. The method of claim 3, wherein the luminescence de-excitation light and the excitation inhibiting light are simultaneously applied to the sample.

5. The method of claim 1, wherein the luminescence excitation light is applied to the sample in pulses.

6. The method of claim 5, wherein the excitation inhibiting light is applied to the sample in pulses or continuously.

7. The method of claim 6, wherein the luminescence de-excitation light is applied to the sample in pulses or continuously.

8. The method of claim 5, wherein the luminescence light is registered at temporal resolution after each pulse of the luminescence excitation light.

9. The method of claim 1, wherein the excitation inhibiting light transfers the luminophore out of the excitable electronic ground state into the protection state by means of a change in conformation.

10. The method of claim 9, wherein the luminophore is a switchable luminophore which is switched off by the excitation inhibiting light.

11. The method of claim 10, wherein the switchable luminophore is a switchable fluorescent protein.

12. The method of claim 9, wherein the sample, in the measurement area, prior to being subjected to the intensity distribution of the excitation inhibiting light, is subjected to an intensity distribution of excitation enabling light transferring the luminophore, at least in the area of the second local minimum of the intensity distribution of the luminescence de-excitation light, into the excitable electronic ground state.

13. The method of claim 1, wherein the excitation inhibiting light, for transferring the luminophore into the protection state, disturbs the excitable electronic ground state of the luminophore in such a way that the luminophore in the protection state has an absorption cross-section for the luminescence excitation light which is reduced by at least a factor of 2 as compared to the undisturbed excitable electronic ground state.

14. The method of claim 13, wherein the electronic ground state of the luminophore is disturbed by a transfer of at least one of impulses and vibrations.

15. The method of claim 14, wherein the impulses or vibrations come from a relaxing modulator entity which is excited by the excitation inhibiting light.

16. The method of claim 13, wherein an atomic order within the luminophore is disturbed in by disturbing the electronic ground state.

17. The method of claim 13, wherein the luminophore, within the disturbed electronic ground state, is not in a thermal equilibrium.

18. A method of high spatial resolution imaging of a structure of a sample, the structure comprising a luminophore, the method comprising
   in a measurement area, subjecting the sample to an intensity distribution of excitation inhibiting light transferring the luminophore out of an excitable electronic ground state into a protection state in which the luminophore is protected against electronic excitation by luminescence excitation light and by luminescence de-excitation light, the intensity distribution of the excitation inhibiting light comprising a first local minimum;
   in the measurement area, subjecting the sample to the luminescence excitation light exciting the luminophore which, within the first local minimum of the intensity distribution of the excitation inhibiting light, is still in its excitable electronic ground state into an excited luminescent state;
   in the measurement area, subjecting the sample to an intensity distribution of the luminescence de-excitation light returning the luminophore out of the excited luminescent state into the excitable electronic ground state, the intensity distribution of the luminescence de-excitation light comprising a second local minimum overlapping with the first local minimum of the intensity distribution of the excitation inhibiting light;

registering luminescence light emitted out of the measurement area;

assigning the registered luminescence light to the position of the second local minimum of the intensity distribution of the luminescence de-excitation light within the sample;

scanning the sample with the second local minimum of the intensity distribution of the luminescence de-excitation light; and repeating the steps of subjecting, registering and assigning for a plurality of positions of the second local minimum of the intensity distribution of the luminescence de-excitation light within the sample.

19. The method of claim 18, wherein the luminophore is a switchable luminophore which is switched off by the excitation inhibiting light.

20. The method of claim 19, wherein the sample, in the measurement area, prior to being subjected to the intensity distribution of the excitation inhibiting light, is subjected to an intensity distribution of excitation enabling light transferring the luminophore, at least in the area of the second local minimum of the intensity distribution of the luminescence de-excitation light, into the excitable electronic ground state.

* * * * *